| United States Patent [19] | [11] Patent Number: 4,499,276 |
|---|---|
| Malhotra et al. | [45] Date of Patent: Feb. 12, 1985 |

[54] REDUCTION OF TRICHLOROMETHYLPYRIDINES TO DICHLOROMETHYLPYRIDINES

[75] Inventors: Sudarshan K. Malhotra, Walnut Creek; Jon A. Orvik, Danville, both of Calif.

[73] Assignee: The Dow Chemical Company, Midland, Mich.

[21] Appl. No.: 475,017

[22] Filed: Mar. 14, 1983

Related U.S. Application Data

[63] Continuation-in-part of Ser. No. 256,863, Apr. 24, 1981, abandoned.

[51] Int. Cl.³ .......................................... C07D 213/26
[52] U.S. Cl. .................................... 546/346; 546/345
[58] Field of Search .............................. 546/346, 345

[56] References Cited

U.S. PATENT DOCUMENTS

| 3,420,833 | 1/1969 | Taplin | 546/180 |
| 3,591,596 | 7/1971 | Wang et al. | 546/294 |
| 4,062,962 | 12/1977 | Noveroske | 424/263 |
| 4,143,144 | 3/1979 | Tobol et al. | 424/263 |
| 4,260,766 | 4/1981 | Morris | 546/303 |

Primary Examiner—Alan L. Rotman
Attorney, Agent, or Firm—S. Preston Jones; Ronald G. Brookens

[57] ABSTRACT

2(6)-(Trichloromethyl)pyridines are reduced to the corresponding 2(6)-(dichloromethyl)pyridines by treatment with a strong base and an anionic reductant derived from a reductant source material selected from the group consisting of chloroform, dimethylsulfoxide, dimethylsulfone, and a ketone having a base-abstractable hydrogen, said treatment taking place in the presence of a polar, non-hydroxylic solvent and/or a phase transfer catalyst.

7 Claims, No Drawings

REDUCTION OF TRICHLOROMETHYLPYRIDINES TO DICHLOROMETHYLPYRIDINES

RELATIONSHIP TO PRIOR APPLICATION

This is a continuation-in-part of application Ser. No. 256,863, filed Apr. 24, 1981 now abandoned.

BACKGROUND OF THE INVENTION (Dichloromethyl) substituted pyridines are known compounds which find utility as pesticides for the control of plant, insect and fungal pests, among others, and as intermediates for preparing compounds having the above utilities. Representative patents which teach such uses include U.S. Pat. Nos. 3,420,833; 3,591,596; 4,062,962 and 4,143,144.

Various derivatives of phenoxypyridine, such as the compounds made from cyano(6-phenoxy(or substituted phenoxy))-2-pyridine methanol, are useful as pesticides. One method of preparing this class of compounds is through an intermediate derivative of alpha-(dichloromethyl)pyridine which is conveniently prepared by reducing the corresponding trichloromethyl derivative.

(Dichloromethyl) substituted pyridines have been prepared from (trichloromethyl) substituted pyridines by a variety of procedures. A few of these procedures include, for example, dehydrochlorination over a palladium catalyst in the presence of formic acid, electrolytic reduction and reductions employing either zinc or stannous chloride with hydrochloric acid and the like. Another method is taught in U.S. Pat. No. 4,260,766 wherein the reduction is conducted with metallic iron or a ferrous iron compound. The prior processes, while producing the desired product, have not found wide success because of one or more shortcomings such as expense of reagents, slow reaction rate, poor selectivity to the desired product or the difficulty in treating waste streams for recycle and/or disposal. The present invention is a process for carrying out the reduction with greater flexibility and specificity than that found using conventional reducing agents.

SUMMARY OF THE INVENTION

The invention herein described is a process for reducing a trichloromethyl substituent in the 2-position of a pyridine ring to a dichloromethyl group which comprises treating said 2-(trichloromethyl)pyridine with a strong base to maintain the reaction under slightly basic conditions and a carbanionic reductant source material selected from the group consisting of chloroform, dialkylsulfoxides, arylalkylsulfones, dialkylsulfones, and ketones, said sulfoxides, sulfones and ketones must have a hydrogen atom on the carbon atom which is alpha to the —C=O, —SO, or —SO$_2$ group; said treatment being carried out in the presence of either a polar, non-hydroxylic solvent and/or a phase transfer catalyst at a temperature of from about −20° C. to about 160° C. for a time sufficient to convert at least some of the trichloromethyl groups to dichloromethyl groups.

As used herein, the term alkyl refers to an alkyl having from one to about four carbon atoms, such as, for example, methyl, ethyl, n-propyl, i-propyl, n-butyl, sec-butyl and t-butyl. The term aryl refers to an aromatic hydrocarbyl group such as, for example, phenyl or tolyl.

In general, (trichloromethyl)pyridine derivatives suitable for use in the process may be represented as follows:

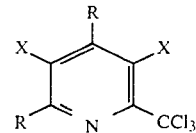

wherein X independently and in each occurrence represents chlorine or hydrogen and R, independently and in each occurrence, represents hydrogen, C$_1$–C$_4$ alkoxy, chlorine, phenoxy, or substituted phenoxy. As used herein, the term substituted phenoxy refers to a phenoxy moiety containing one or more substituents which do not detrimentally affect the reduction of the trichloromethyl group. Such a substituted phenoxy moiety may contain one or more substituents such as, for example, alkyl, alkoxy, or halo.

Representative (trichloromethyl)pyridines which can be employed in the practice of the present invention include, among others 2-chloro-6-(trichloromethyl)pyridine,
2-chloro-4-methoxy-6-(trichloromethyl)pyridine,
3,5-dichloro-2-(trichloromethyl)pyridine,
4,6-dichloro-2-(trichloromethyl)pyridine,
3,4,5,6-tetrachloro-2-(trichloromethyl)pyridine,
6-phenoxy-2-(trichloromethyl)pyridine,
6-(4-chlorophenoxy)-2-(trichloromethyl)pyridine
6-(3-chlorophenoxy)-2-(trichloromethyl)pyridine
6-(4-fluorophenoxy)-2-(trichloromethyl)pyridine,
6-phenoxy-5-fluoro-2-(trichloromethyl)pyridine,
and 6-(4-methoxyphenoxy)-2-(trichloromethyl)pyridine.

As used herein, the term polar, non-hydroxylic solvent refers to those solvents which provide sufficient solubility for the reactants to function as a medium for the reaction. A number of readily available polar, non-hydroxylic solvents has been found suitable for use in this process, such as, for example, N-methylpyrrolidone, dimethylformamide, dimethysulfoxide, hexamethylphosphoric triamide and diglyme.

Normally, instead of using a polar, non-hydroxylic solvent, a quaternary ammonium phase transfer catalyst may be used. A number of quaternary ammonium phase transfer catalysts suitable for use in the process are commercially available. Those skilled in the art are familiar with such catalysts—for example, tetra-n-butylammonium chloride, methyl tri-n-butylammonium chloride and benzyl triethylammonium chloride.

In carrying out the process of the present invention, the reduction is carried out at a temperature of from about −20° C. to about 160° C., with a temperature range of from about 0° C. to about 40° C. being preferred. At temperatures below about −20° C. the reduction proceeds so slowly that it would not be commercially feasible to carry it out. At higher temperatures appreciable degradation of the reactants and desired products tends to occur. Generally, when the more reactive reductants and/or more reactive (trichloromethyl)pyridine compounds are employed, the reaction can be simply carried out at ambient temperatures. The pressure at which the reaction occurs is not critical, and usually the process is performed at atmospheric pressure.

In carrying out the reduction using a ketone, a number of ketones are suitable including, for example, acetone, methylethyl ketone, and acetyl acetone. The only limitation on the operable ketones is that they must have a base abstractable hydrogen.

The strong base is either an inorganic base such as an alkali metal hydroxide (sodium, potassium, lithium or cesium hydroxide) or an organic base such as, for example, choline, a compound of the formula $(CH_3)_3N^{\oplus}-CH_2-CH_2OH/OH^{\ominus}$ or alkali metal alkoxides such as sodium methoxide. Of the above bases, sodium hydroxide and potassium hydroxide are preferred.

A solvent is not always necessary for the reaction to proceed and if the pyridine reactant or the reducing agent can also act as the solvent, the reaction may be carried out in the absence of additional solvent, ordinarily by the inclusion of a phase transfer catalyst in the reaction mixture.

The process of the present invention may be carried out as a batch process in which case it is preferred that the various reactants be present in about equimolar amounts. The process may also be carried out in a manner wherein reaction mixture is continuously removed and more reactants continuously added.

Chloroform is a readily available reducing agent which has shown good selectivity in the process and as such is utilized in one preferred embodiment of the invention. It has been found that when chloroform is used as the reductant source material, an equilibrium occurs with one of the products formed being carbon tetrachloride. The removal of the carbon tetrachloride formed will therefore drive the desired reaction to completion, resulting in more product being produced.

The following examples will serve to further illustrate the invention, but should not be interpreted as a limitation thereon.

EXAMPLE 1

2-Chloro-6-(trichloromethyl)pyridine (2.31 grams, 0.01 mole) was added along with 20 ml of chloroform to a reaction vessel. Aqueous sodium hydroxide (3 ml of 50% NaOH by weight) and one milliliter of phase-transfer catalyst (tricaprylylmethyl ammonium chloride (available from Aldrich Chemical as "ADOGEN-464 which is the registered trademark of Archer Daniels Midland Co.)) were added to the reaction mixture. The organic phase was sampled at intervals for gas/liquid chromatography (glc) analysis. The following results were obtained as area percent glc:

| Time | —CHCl$_2$ Compound | —CCl$_3$ Compound |
|---|---|---|
| 5 min. | 12 | 82 |
| 40 min. | 18 | 73 |
| Overnight | 64 | 24 |

EXAMPLE 2

Into a reaction vessel containing 2.31 grams of 2-chloro-6-(trichloromethyl)pyridine (0.01 mole) dissolved in 20 ml of N-methylpyrrolidone was added at room temperature 1.5 grams of powdered 85% grade potassium hydroxide pellets (0.023 mole). Chloroform (5 ml, 0.063 mole) was added to the mixture. Within three minutes the reaction was observed by glc analysis to come to equilibrium. Analysis indicated that 34% of the trichloromethyl starting material had been reduced to the dichloromethyl product.

EXAMPLE 3

A mixture of 30 grams of 6-phenoxy-2-(trichloromethyl)pyridine, 16 grams of 85% KOH pellets and 50 ml of H$_2$O in 200 ml of dimethyl sulfoxide was heated at 70°–80° C. for 1.5 hour. 30 ml of glacial acetic acid was added, the mixture diluted with water and extracted with CH$_2$Cl$_2$. The extract was washed with water, dried and concentrated to 22 grams of a brown oil which was shown by glc and nmr (nuclear magnetic resonance) to be 90% pure 2-chloro-6-(dichloromethyl)pyridine. The calculated yield of the latter compound was 75%.

EXAMPLE 4

(a) Reduction of 6-phenoxy-2-(trichloromethyl)pyridine in N-methylpyrrolidone with 2 molecular proportions of dimethylsulfone and 3.6 molecular proportions of KOH for about 2 hours at about 155° C., resulted in complete conversion of the trichloromethyl group and a 50% yield, based on conversion, of the desired dichloromethyl compound.

(b) Under otherwise the same conditions as in (a), 6-chloro-2-(trichloromethyl)pyridine exhibited rapid reduction at 100° C., upon standing, the product degraded.

EXAMPLE 5

(a) GLC analysis of the reaction mixture obtained by reacting 2.65 grams of 4,6-dichloro-2-(trichloromethyl)-pyridine in 20 ml of diglyme with 5 ml of CHCl$_3$ and 0.5 gram of powdered KOH for 5 minutes at a temperature of 29°–33° C. gave a 56.4/43.0 area percent ratio for the trichloromethyl starting compound and the corresponding dichloromethyl derivative.

(b) GLC analysis of the reaction mixture obtained by reacting 3,4,5,6-tetrachloro-2-(trichloromethyl)pyridine (3.34 grams) in 20 ml of N-methylpyrrolidone with 5 ml of CHCl$_3$ and 0.55 gram of KOH for twenty-five minutes at a temperature of 28.5°–34° C. gave a 56.0/38.5 area % ratio for the trichloromethyl starting compound and the corresponding dichloromethyl derivative.

EXAMPLE 6

2-Chloro-6-(trichloromethyl)pyridine, 2.31 grams (0.01 mole) was added along with about 15 ml of N-methylpyrrolidone to a reaction vessel. Aqueous sodium hydroxide (2.1 grams of 50% NaOH by weight) and 2 drops of ADOGEN-464 were added to the reaction mixture. To the mixture at 25° C. was added 1.0 ml of acetone. The mixture was heated at a temperature of from 25° C. to 70° C. over a period of about 1 hour. The organic phase was sampled at intervals for gas/liquid chromatography (glc) analysis. The following results were obtained as area percent glc:

| Time | —CHCl$_2$ Compound | —CCl$_3$ Compound |
|---|---|---|
| 10 min. | 39 | 61 |
| 25 min. | 80 | 17 |
| 50 min. | 89 | 7 |

EXAMPLE 7

2-Chloro-6-(trichloromethyl)pyridine, 2.31 grams (0.01 mole) was added along with 20 ml of diglyme to a reaction vessel. To the mixture, at a temperature of 22° C., was added 0.5 grams of KOH and 5 ml of acetone. A mild exotherm was observed. After about 40 minutes of reaction time an additional 0.6 grams of KOH was added. The organic phase was sampled at intervals for gas/liquid chromatography (glc) analysis. The following results were obtained as area percent glc:

| Time | —CHCl$_2$ Compound | —CCl$_3$ Compound |
| --- | --- | --- |
| 8 min. | 5 | 95 |
| 40 min. | 35 | 65 |
| 79 min. | 55.3 | 39.2 |
| 110 min. | 59 | 30 |
| 175 min. | Degradation | |

For a repeat of this run, the reaction would be terminated after 110 minutes.

What is claimed is:

1. A process for reducing the trichloromethyl group in a (trichloromethyl)pyridine compound to a dichloromethyl group which comprises treating said compound with a strong base and a reductant source material selected from the group consisting of chloroform, dialkylsulfoxides, arylalkylsulfones, dialkylsulfones and ketones wherein each alkyl group is of from one to four carbon atoms and the term aryl represents phenyl or tolyl, said sulfoxides, sulfones and ketones must have a hydrogen atom on the carbon atom which is alpha to the —C=O, —SO, or —SO$_2$ group, said ketones must also have a base abstractable hydrogen, said treatment being carried out in the presence of a polar, non-hydroxylic solvent providing sufficient solubility for the reactants and/or a quaternary ammonium phase transfer catalyst at a temperature of from about −20° C. to about 160° C. for a time sufficient to convert to the corresponding (dichloromethyl)pyridine compound.

2. The process of claim 1 wherein the reaction is carried out at a temperature of from about 0° to about 40° C.

3. The process of claim 1 wherein the strong base is sodium hydroxide.

4. The process of claim 2 wherein the trichloromethyl substituent is reduced using chloroform as the reductant source material and sodium hydroxide as the strong base.

5. The process of claim 1 wherein said (trichloromethyl)pyridine compound is 6-chloro-2-(trichloromethyl)pyridine.

6. The process of claim 1 wherein said (trichloromethyl)pyridine compound is 6-phenoxy-2-(trichloromethyl)pyridine.

7. The process of claim 5 wherein sodium hydroxide is employed as the strong base, chloroform is employed both as the reductant source material and the reaction medium and the reaction is carried out in the presence of a quaternary ammonium phase transfer catalyst.

* * * * *